United States Patent [19]

Lundahl

[11] Patent Number: 4,998,930

[45] Date of Patent: Mar. 12, 1991

[54] INTRACAVITY LASER PHOTOTHERAPY METHOD

[75] Inventor: Scott L. Lundahl, Moraga, Calif.

[73] Assignee: Phototherapeutic Systems, Martinez, Calif.

[21] Appl. No.: 374,664

[22] Filed: Aug. 4, 1989

Related U.S. Application Data

[63] Continuation-in-part of Ser. No. 227,751, Aug. 3, 1988, abandoned.

[51] Int. Cl.[5] .............................................. A61B 17/36
[52] U.S. Cl. ...................................... 606/15; 128/395
[58] Field of Search .................................... 606/13–16; 128/395–398

[56] References Cited

U.S. PATENT DOCUMENTS

| | | | |
|---|---|---|---|
| 4,320,745 | 3/1982 | Bhitiyakul et al. | 128/11 |
| 4,612,938 | 9/1986 | Dietrich et al. | 606/15 |
| 4,784,133 | 11/1988 | Mackin | 606/7 |
| 4,799,479 | 1/1989 | Spears | 606/28 |

*Primary Examiner*—Max Hindenburg
*Attorney, Agent, or Firm*—Douglas E. White

[57] ABSTRACT

A method is disclosed for the uniform irradiation of the inner wall of a hollow organ, including the steps of inserting a catheter having a deflated translucent balloon into the interior of the organ; inflating the balloon until it forms a predetermined configuration and distends the inner wall of the organ to be irradiated into a contiguous and congruent configuration; inserting a light transmission fiber having an isotropic light diffuser tip into the catheter so that the tip is positioned at the center of the balloon and, hence, automatically positioned at the center of the wall to be irradiated; and transmitting light through the fiber out the tip whereby light of uniform intensity irradiates the wall.

19 Claims, 1 Drawing Sheet

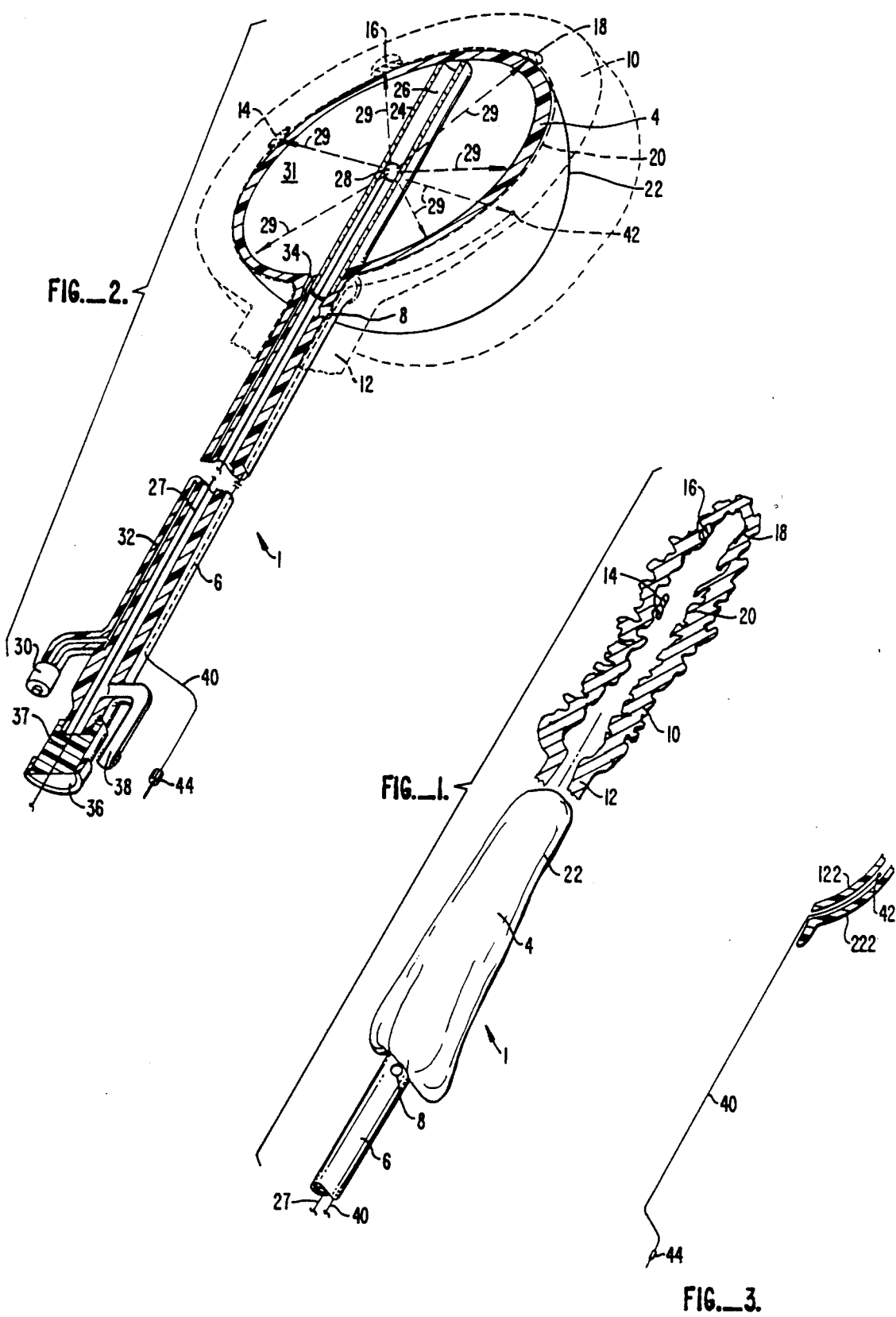

INTRACAVITY LASER PHOTOTHERAPY METHOD

RELATED APPLICATION

This application is a continuation-in-part of applicant's application Ser. No. 07/227,751, filed Aug. 3, 1988, entitled INTRACAVITY LASER PHOTOTHERAPY METHOD AND CATHETER APPARATUS, now abandoned.

FIELD OF THE INVENTION

This invention relates to a method and apparatus for the uniform irradiation of body cavities through distension of the cavity into a uniform shape, more particularly to a balloon catheter having a light sensor in the balloon wall which forms a human body cavity into a uniform shape, such as a sphere, for laser therapy.

BACKGROUND OF THE INVENTION

It goes without saying that cancer is a feared and life-destroying disease. Countless resources and endless research have been directed toward the development of effective treatment of this disease.

Rather than use invasive methods such as surgery, it has been known to apply laser irradiation to destroy cancer cells residing on the internal surface of organs, such as human urinary bladders.

Prior developments in this field will be generally illustrated by reference to the following patents:

| Patent No. | Patentee | Issue Date |
| --- | --- | --- |
| 4,470,407 | H.M.G. Hussein | 09/11/84 |
| 1,089,805 | G. Wolf | 03/10/14 |
| 4,693,556 | J.S. McCaughan | 09/15/87 |
| 4,676,231 | H. Hisazumi et al. | 06/30/87 |
| 4,313,431 | F. Frank | 02/02/82 |
| 4,612,938 | R. Dietrich et al. | 09/23/86 |
| 4,512,762 | J.R. Spears | 04/23/85 |
| 4,723,556 | M.L. Sussman | 02/09/88 |

One method of treatment has been to attempt to direct laser light radiation only on the tumors. Hussein in U.S. Pat. No. 4,470,407 and Frank in U.S. Pat. No. 4,313,431 teach devices utiliZing this method. Devices such as those of Hussein and Frank comprise endoscopic apparatus having optical viewers whereby the physician can look at the interior of the cavity and manipulate the position of the tip of a laser light transmitting fiber so that a relatively focused beam of radiation is directed toward the visible cancer tissue. This method does not teach positioning the tip of the laser fiber centrally within the cavity because it does not contemplate the uniform irradiation of the entire inner cavity surface at one time. One problem with this method is that it is effectively limited to the treatment of visible cancers.

On the other hand, photodynamic therapy is a relatively recently developed curative procedure whereby a dye-like photoactivating drug, such as a hemotoporphyrin derivative (HpD) is taken into tumors by oral administration or by injection. Laser irradiation of the entire interior of the diseased organ selectively destroys the tumors through a photochemical reaction, but could harm healthy tissue if it is not performed properly. Even microscopic cancers can be treated, since the radiation does not need to be focused away from healthy tissue because the healthy tissue has very little or no photoactivating drug.

Successful treatment requires that the dosage be uniform. Over-irradiation of healthy tissue causes "hot spots" or burn regions in healthy tissue. Under-irradiation results in "cool spots" wherein there is less than complete necrosis of the cancerous tissue, which may then reappear at a later time.

McCaughan in U.S. Pat. No. 4,693,556, Hisazumi et al. in U.S. Pat. No. 4,676,231, and Dietrich et al. in U.S. Pat. No. 4,612,938 teach attempts to irradiate the entire cavity by adding light diffusing means somewhere between the laser fiber tip and the inner cavity wall. This approach recognizes that the light directed at the cavity wall must be uniform so that hot and cool spots will not occur at different areas of the wall. Dietrich et al. teach the use of a balloon catheter which is filled with a light scattering or dispersing medium for this purpose.

Hussein also teaches the use of a balloon catheter, in this case to displace opaque fluids away from the tumor viewing means. Spears, in U.S. Pat. No. 4,512,762, teaches a balloon catheter which expands to conform to the irregular surface of an artery affected by atherosclerosis.

However, this art only addresses the problem of disseminating spherically uniform radiation away from the laser fiber tip. These teachings do not solve the problem of ensuring that the cavity wall itself receives the radiation in a uniform manner. This requires that all of the irradiated tissue be located at essentially the same distance from the light source. In the prior art, this is usually roughly accomplished by attempting to position the laser fiber tip in the center of the cavity of the organ through use of external ultrasonic wave positioning apparatus as taught by Hisazumi. The balloon of Dietrich et al., being much smaller than the cavity, must be similarly positioned.

This solution is unsatisfactory because, first of all, the tip may move and have to be continually repositioned. More importantly, however, is the fact that an organ, such as a bladder (even when full), will not be of uniformly spherical shape. A laser diffuser tip which fortuitously might be positioned in the exact center of gravity of a non-spherical body still would not result in uniform irradiation, since parts of the cavity wall will be significantly farther away from the tip than others and, hence, receive a smaller dose. There is no known diffusing medium which will completely compensate for the non-uniform dosages which result from spatial disparities.

This problem is exacerbated by the fact that the intensity of radiation is inversely proportional to the square of the distance from its source. Even a slight asymmetry in the bladder's shape will result in unacceptably large differences in dosages and could cause a dangerous incidence of under-irradiated cool spots and over-irradiated hot spots.

Therefore, there exists a need to provide uniform illumination at the organ's surface during photodynamic therapy, which need has been unsatisfactorily addressed in the existing art through the emphasis in the art on uniformity only at the radiation source.

SUMMARY OF THE INVENTION

The present invention is a catheter which has a balloon on its end which forms a sphere or other uniform shape when inflated with fluid due to uniform pressure exerted on its wall by the inflation fluid and due to a center tube which holds the balloon wall to a fixed length. When the balloon is inserted into, for example, a bladder and inflated, the bladder is likewise forced into a spherical shape. An optical laser fiber with an isotropic diffuser tip may then be placed inside the balloon and held at its exact center by the catheter tube. The balloon is preferably translucent rather than transparent, so the light which passes thorough it is further diffused during phototherapy. The cells to be treated press against the outside of the balloon and all therefore are equidistant from the diffuser tip. Hence, all cells receive an equal dose of light.

An optical sensing fiber is preferably affixed to or within the wall material of the balloon to measure intensity and accumulated light dose at the organ wall. This sensor may also be used to determine the concentration of photoactivating drug in the cells lining the cavity or organ wall by measuring the induced fluorescence of the drug.

Ports for filling and draining fluid are included.

In its broadest form, the invention would comprise any translucent or transparent catheter with means for holding the cells to be treated by phototherapy at a fixed distance from an optical fiber light source. One could design balloon catheters for use in phototherapy of hollow cavities of the human body other than the bladder, such as the brain, the stomach, the intestines and the vagina. For example, one could conceive of a cylindrical (rather than spherical) balloon wherein the diffuser tip is slowly drawn along its central axis in order to uniformly expose cells in organs which may be forced into cylindrical shapes, such as an esophagus or an artery. Alternatively, the diffuser in such a device could itself be cylindrical in order to create radiation that is radially uniform about its axis. While cylindrical balloon catheters are known, none incorporate in the balloon wall the unique optical sensing fiber of the present invention.

FEATURES AND ADVANTAGES

An object of this invention is to provide a method of laser phototherapy which causes complete necrosis of surface-existing tumors on a body cavity wall through distension of the wall into a uniform shape, whereby radiation of uniform intensity and duration may be applied. Particularly, a method of treating cancer cells in the human urinary bladder, brain, or esophagus containing concentrations of a photoactivating drug is disclosed.

Another object of the present invention is to provide an apparatus capable of said cavity distension and shaping. The apparatus disclosed is also capable of automatically positioning an isotropic diffuser tip at the center of the cavity and securely holding it there during irradiation.

A further object is to disclose a balloon catheter which distends the inner wall of a normally asymmetric human organ or cavity, such as a urinary bladder, and shapes it into a sphere for irradiation with uniform illumination by a diffuser automatically positioned at the center of the sphere. This feature limits the need for costly and time consuming cystoscopic and ultrasonic positioning of the light source within the bladder prior to or during laser therapy.

Yet another feature is that one balloon disclosed is formed of a non-distensible or minimally distensible translucent plastic material such as polyurethane which forms a semi-rigid resilient sphere (i.e. it resists deformation and tends to return to a spherical shape if deformed) when filled with fluid or gas. In the case of a balloon catheter made of non-distensible or minimally distensible material, the cavity or organ is shaped into a perfect or nearly perfect sphere, as opposed to the generally spherical shape achieved by distensible or elastic balloons.

Yet another object is to assure accurate light dosimetry. Disclosed is an optical sensing fiber in the wall of the balloon for continuous monitoring of the light illuminating the bladder wall and for providing an accurate measurement of the cumulative light dose to which the bladder wall is exposed. The optical sensing fiber can be used in balloon catheters of other than spherical shape, i.e. cylindrical catheters. The sensing fiber preferably senses light at its tip, but could be adapted to sense it elsewhere.

An object of the invention is to provide ports for filling the balloon of the catheter and for draining fluid from the bladder or other hollow viscus as the procedure is performed.

Also disclosed is a non-distensible or minimally distensible center tube in the balloon which assists in distending the bladder into a sphere and in holding the laser diffuser tip in the center thereof.

A further object is to disclose a method of measuring the concentration of photoactivating drug present in the bladder wall by measuring with one or more optical sensing fibers in the wall of the balloon the fluorescent spectrum emitted by the drug during excitation by light.

Other novel features which are characteristic of the invention, as to organization and method of operation, together with further objects and advantages thereof will be better understood from the following description considered in connection with the accompanying drawing in which a preferred embodiment of the invention is illustrated by way of example. It is to be expressly understood, however, that the drawing is for the purpose of illustration and description only and is not intended as a definition of the limits of the invention.

Certain terminology and derivations thereof may be used in the following description for convenience in reference only and will not be limiting. For example, the words "upwardly," "downwardly," "leftwardly," and "rightwardly" will refer to directions in the drawings to which reference is made. The words "inwardly" and "outwardly" will refer to directions toward and away from, respectively, the geometric center of a device and designated parts thereof.

BRIEF DESCRIPTION OF THE DRAWING

FIG. 1 is a fragmentary part sectional perspective view of the deflated intracavity laser catheter of this invention showing the method of inserting it into a urinary bladder;

FIG. 2 is a fragmentary sectional perspective view of the catheter of FIG. 1 showing the method of distending the bladder or other hollow viscus into a sphere and irradiating it during phototherapy; and FIG. 3 is part schematic, part broken sectional view showing the optical sensing fiber sandwiched between a double wall balloon catheter.

DRAWING REFERENCE NUMERALS 1 catheter
4 balloon
6 stem
8 drainage port 10 hollow organ
12 neck of 10
14 papillary tumor
16 invasive disease
18 carcinoma-in-situ
20 inner wall of 10
22 outer wall of 4
24 center tube of 4
26 inner lumen
27 quartz fiber
28 isotropic diffuser tip
29 laser light radiation
30 inflation port
31 inflation medium
32 inflation lumen
34 inflation outlet
36 nipple or bushing
37 through hole
38 drainage outlet
40 optical sensing fiber
42 tip of 40
44 SMA connector to 40
122 first inner wall of 4
222 second outer wall of 4

DESCRIPTION OF A PREFERRED EMBODIMENT

Referring to FIG. 1, there is illustrated therein the catheter insertion step of the laser phototherapy method and the intracavity laser catheter apparatus 1 of the present invention. While the method and the apparatus used to practice the method may be used in the treatment of a variety of organs or cavities, their use in conjunction with the human bladder will be discussed, by way of illustration.

The catheter 1 comprises a balloon 4 on its distal end, which is the upper end of the catheter as shown in FIG. 1. The balloon 4 has an outer wall 22 and is shown deflated in FIG. 1 for insertion into a hollow organ 10, for example, a human urinary bladder having a bladder neck 12 and connected to the patient's urethra (not illustrated). The balloon 4 may be transparent to laser light, but is preferably translucent in order that received diffused laser light is further diffused upon transmission through the balloon wall 22.

The balloon 4 is sealed to the upper end of a flexible stem 6. The catheter 1 is inserted through the urethra and passed upwardly until it enters the bladder 10 via the neck 12. The catheter 1 may be inserted through use of a hand-directed sheath of known type. To be able to pass through the sheath and also to be able to pass around internal bodily obstructions, the catheter is preferably flexible throughout its penetrating length.

The bladder is shown with three types of lesions. Some of these may be microscopic in size but are drawn enlarged for purposes of clarity of illustration. A typical papillary tumor 14 projects outwardly from the inner bladder wall 20. Also illustrated are a pre-malignant lesion 18 of the bladder's lining, i.e. carcinoma-in-situ, and an invasive lesion 16 of the bladder wall, the latter of which begins on the inner surface of the bladder 10 and invades deeply into the bladder wall. Tumors 14, 16, 18 and the multitude of other similar tumors likely to be present have previously concentrated a photoactivating drug through intravenous administration or other means.

Turning to FIG. 2, the process of laser irradiation of tumors 14, 16, 18, is therein illustrated. Once the balloon 4 on the upper distal end of catheter 1 is fully within the bladder cavity, it is filled with fluid or gas 31, typically a simple saline solution, although a light dispersing medium may be substituted as taught in the art. Stem 6 contains at least two separate lumens or hollow tubes, inner lumen 26 and inflation lumen 32. The balloon inflation medium 31 is pumped into inflation lumen 32 via inflation port 30 projecting outwardly transverse to the axis of the stem. The medium enters the balloon through inflation port 34 which opens into the balloon interior. When the phototherapy procedure is complete, the medium may be withdrawn via the same route.

The inflation port 30 is fitted with a standard one-way valve assembly so that the inflation fluid 31 can be retained in the balloon under significant pressure. This pressure forces the balloon, when constructed of a translucent minimally distensible plastic material such as polyurethane, to form a perfect or nearly perfect sphere even against the internal forces which normally cause the organ or cavity to be other than spherical, even when the bladder is full.

The method may be practiced with a distensible or elastic balloon. While the organ may not be formed into a perfect sphere by an elastic balloon, due to pressure from surrounding tissue, the shape will tend toward the spherical and this represents a significant improvement over methods which do not try to shape the organ or cavity at all. It may be somewhat difficult, however, to construct a balloon of the size of the bladder 10 out of non-distensible material and still insert the balloon through the narrow urethra. It is anticipated, therefore, that the method will be most successfully practiced with non-distensible balloons in small cavities, such as those formed when brain tumors are removed by surgery, and that elastic balloons will be used, at least initially, for treating the bladder. Nevertheless, the construction and use of non-distensible balloons in large cavities, such as the bladder, remains within the spirit and scope of this invention as defined by the appended claims.

The outer wall 22 of a one or more layer balloon 4 presses firmly against the inner wall 20 of the bladder, also distending it into a sphere and perhaps stretching it somewhat. Different size balloons can be selected, depending on the size of bladder or other hollow viscus to be encountered, to ensure that the organ assumes the intended shape However, even if the bladder is less than fully distended, it will be clear that it still will be formed into a sphere since that is the only shape the balloon may form unless it encounters significant opposing forces (from, e.g., skeletal tissue) which are not expected.

A flexible clear plastic, but preferably minimally distensible, center tube 24 is affixed to the upper end of the stem 6, traverses an exact diameter of the balloon, and is fixedly attached to the inner surface thereof at a point directly opposite the stem. The stem 6 and center tube 24 are preferably flexible so that the device may be maneuvered through the urinary tract during insertion. The flexible center tube 24 and stem 6 may be passed over a commonly available catheter guide to facilitate passage through the curved male urethra. To perform this function, the catheter guide will be passed into the catheter's inner lumen 26. Although the center tube 24 is flexible, its connection to the balloon wall ensures that it is drawn taut and straight after the balloon is inflated.

This ensures that the isotropic laser light diffuser tip 28 (discussed below) located at the midpoint of the tube 24 is positioned accurately in the spherical center of the balloon along a diameter thereof. The center tube also further conforms the balloon into the desired spherical shape. Insofar as the balloon and the bladder are forced into contiguous congruent spheres, the light diffuser tip is automatically positioned at the center of the bladder cavity and is equidistant from all points on the inner wall 20 of the bladder.

The inner lumen 26 traverses the center axis of the stem 6 and extends through the central axis of the center tube 24. At the lower proximal end of the stem is a nipple or bushing 36 having a through hole 37. The nipple 36 is designed to allow the insertion and passage of a quartz laser light transmission fiber 27, but to prevent leakage of air and fluids, since the inner lumen 26 also serves as a drainage line for urine or other body secretions that may collect in the bladder 10 during treatment. However, an additional separate drainage lumen could easily be added. Drainage outlet 38 leads transversely outward from the lower end of inner lumen for draining fluid out of the organ from one or more drainage ports 8, which lead transversely outward from the upper end of the inner lumen just before the point of attachment of the balloon so that they are located within the bladder during the procedure.

The quartz or other laser light transmission fiber 27 is shown schematically as a dimensionless line. However, it will typically have known cladding and an outer ensheathing jacket or coating (not illustrated). There is associated optical coupling at the lower end of laser fiber 27 for connection to a surgical laser.

The diffuser tip 28 is located at the upper light output end of the light conducting fiber 27 which extends axially through the inner lumen 26 to the midpoint of the center tube 24. It is anticipated that the fiber 27 and associated diffuser 28 will be inserted into the catheter after it is in place in the bladder and the balloon is inflated. Alternatively, the fiber 27 could be inserted into the catheter before the latter is inserted into the bladder without altering the method or the effect of treatment. The diffuser may be precisely positioned at the midpoint of tube 24 by marking the fiber at a point equaling the length of the stem plus one half the length of the center tube and aligning the mark with the outer edge of the nipple 36. Alternatively, a stop could be incorporated at the midpoint of the center tube to engage the diffuser tip 28 when in the correct position.

Upon activation of the external laser, light 29 is radiated isotropically from tip 28 in a spherical pattern and with uniform intensity at points radially equidistant from the diffuser tip. Even points on the inner bladder wall 20 which are located to the rear of the tip are effectively irradiated.

Since the balloon wall 22 forms an optical interface between the light source 28 and the bladder wall 10, both forward transmission and back reflection occur. The back reflection component of the light flux is then distributed on the balloon's inner surface area via a phenomenon known as the integrating sphere effect. This will produce a more even light distribution than could be achieved with a laser catheter or other light emitting or scattering device which did not incorporate a spherical balloon.

Distension of the bladder wall will unfold the normal folds of the bladder mucosa and allow light to reach the entire mucosal covering of the bladder wall. Tumors 14, 16, and 18 are pressed against the outer wall 4 of the balloon and are all, therefore, equidistant from the diffuser tip 28. The three dimensional papillary tumor 14 is flattened by the balloon, as are other surface irregularities present in the wall of the bladder, thus allowing improved light penetration of these areas. Tumors 14, 16, and 18 all receive the same dosage since light intensity varies only with the distance from the source.

Methodologies as taught in the prior art cannot photoirradiate tissue to a depth greater than the natural extinction depth for the wavelength of light used for treatment. However, the methodology presented here will make it possible to photoirradiate papillary tumors 14 to depths greater than can be achieved by current systems. Even though the penetration depth of the light remains the same, the volume of tumor treated will be increased because compressing the tumor with the expanded balloon temporarily makes it thinner during the treatment process.

The laser is activated for the length of time previously calculated to be necessary to cause that photochemical reaction within tumors 14, 16, 18 which will result in their complete destruction without, at the same time, overexposing healthy adjacent cells.

Concurrently, the process may be monitored in the event the activation period needs to be varied once the procedure has begun. An optical sensing fiber 40 is capable of measuring radiation received at its tip 42. The sensing fiber 40 leads up the stem 6 (preferably through a third stem lumen) and is preferably sandwiched between the inner 122 and outer 222 walls of a two layer balloon, as best seen in the fragmentary sectional view of FIG. 3.

Sensing fiber 40 leads out the bottom of nipple 36, via standard SMA connector 44 to known or readily assembled controlling/monitoring detector apparatus (not illustrated) for measurement of dosage, e.g., a high sensitivity photomultipler or photodiode with associated filters, amplifiers and readouts. The sensor tip 42, being positioned in very close proximity to the inner wall 20 of the bladder as it is irradiated, allows continuous monitoring of the light illuminating the bladder wall and provides an accurate measurement of the cumulative light dose to which it is exposed. Light power output is also monitored and alarm may be given in the event of abnormal light conditions.

The output signal from the sensing fiber 40 is proportional to the actual light fluence reaching the organ wall because the sensing fiber is embedded into the balloon wall and is in close proximity, as described above, to the organ wall. This output signal can be used by an external apparatus to continuously and automatically adjust the magnitude of treatment light (normally laser light) or the duration of output from the treatment light source to compensate for variations in the output of the light source during treatment. This feature will permit accurate light dosimetry irrespective of variations in the treatment light source. Since the proportionality ratio for the sensing fiber will be known at the time of treatment, this technique provides a form of "closed loop feedback". It is not taught in the prior art.

When a photoactivating drug is excited by light 29 of an appropriate wavelength, the drug emits a characteristic fluorescent spectrum. It has been shown that the amplitude of this spectrum is directly proportional to the concentration of drug present in tissue, such as tumors 14, 16, 18.

By exciting the photoactivating drug with the light diffusing quartz fiber 27 and by measuring of the resultant fluorescence spectrum via one or more optical sensing fibers 40 incorporated onto or into the material of the balloon of the laser catheter 1, it is possible to determine the concentration of photoactivating drug present in the bladder wall or other tissue being treated by phototherapy. Overall or average concentrations throughout the wall may be measured. Alternatively, concentrations at a specific point may be measured, for example, with a shielded sensing fiber.

This information is then used to adjust the light dosage prior to and/or during treatment to compensate for individual variations in drug uptake in the tissues being treated. It can also be used to determine the maximum dose acceptable to the healthy tissue, or for other purposes. This method will greatly enhance the accuracy of phototherapy.

Forcing the hollow organ 10 to itself form a sphere, which is capable of receiving radiation at uniform dosage throughout its inner surface, is a principal feature of this invention and nowhere suggested in the art.

Another principal feature is the addition of sensing fibers in the balloon wall, which feature is also not found in the art, even in cylindrical balloon catheters. Thus, this invention may be practiced with balloons of differing shape, for example, cylindrical balloons having tubular light diffusers that could be used to press an artery, an esophagus, or the like, into a cylindrical shape for uniformly receiving and monitoring radial radiation. The essential characteristic of the shape of the balloon is that it be capable of distending at least one portion of an inner wall of the cavity to be irradiated into a surface all points on which are equidistant from a line or point in space. In the case of a cylindrical catheter, the line will be the axis of the cylinder. In the case of a spherical catheter the point will be the center of the sphere.

The above process for whole bladder phototherapy may be modified and the invention practiced in partial bladder phototherapy. In the latter procedure, segments of the balloon 4 may be covered with or manufactured from an opaque material so that the overlying sections of the bladder will not be exposed to light. This feature will allow high risk areas of the bladder to be treated with phototherapy, through the transparent or translucent portion of the balloon wall 22, while sparing areas of the bladder wall 20 which may not contain malignant or premalignant lesions.

While the above provides a full and complete disclosure of the preferred embodiments of this invention, various modifications, alternate constructions, and equivalents may be employed without departing from the true spirit and scope of the invention. For example, the center tube 24 could be retractable within the stem 6 rather than attached to the inner surface of the balloon wall. Therefore, the above description and illustrations should not be construed as limiting the scope of the invention which is defined by the appended claims.

I claim:

1. A method for the uniform irradiation of the inner wall of a hollow cavity, including the steps of:
   (a) providing a catheter having a deflated translucent balloon, the balloon having a wall;
   (b) inserting the catheter into the interior of the cavity;
   (c) inflating the balloon until the balloon wall forms a generally spherical balloon configuration and distends at least one portion of an inner wall of the cavity to be irradiated into a contiguous and congruent generally spherical cavity configuration;
   (d) inserting a light transmission fiber having a light diffuser tip into the catheter so that the tip is positioned at a center of the inflated balloon and, hence, automatically positioned at a uniform distance from the at least one portion of the cavity wall to be irradiated; and
   (e) transmitting light through the transmission fiber out the tip
      (e-1) whereby light of uniform intensity irradiates the at least one portion of the cavity wall.

2. The method of claim 1 wherein
   (a-1) the balloon is made, in step (a), of minimally distensible material and
   (c-1) the cavity is a human viscus, at least one portion of which cavity is formed in step (c) into a nearly perfectly spherical cavity configuration.

3. A method for the uniform irradiation of the inner wall of a hollow cavity, including the steps of:
   (a) providing a catheter having a deflated translucent balloon, the balloon having a wall;
      (a-1) providing, in step (a), at least one optical sensing fiber at the wall of the balloon;
   (b) inserting the catheter into the interior of the cavity;
   (c) inflating the balloon until the balloon wall forms a generally spherical balloon configuration and distends at least one portion of an inner wall of the cavity to be irradiated into a contiguous and congruent generally spherical cavity configuration;
   (d) inserting a light transmission fiber having a light diffuser tip into the catheter so that the tip is positioned at a center of the inflated balloon and, hence, automatically positioned at a uniform distance from the at least one portion of the cavity wall to be irradiated;
   (e) transmitting light through the transmission fiber out the tip
      (e-1) whereby light of uniform intensity irradiates the at least one portion of the cavity wall; and
   (f) monitoring with the sensing fiber on the wall of the cavity the light to which the sensing fiber and, hence, the cavity wall are exposed.

4. The method of claim 3, further including:
   (a-2) providing, in step (a), a transparent minimally distensible center tube extending the length of the balloon through the center of the balloon for positioning the tip at the center of the balloon when the balloon is inflated in step (c).

5. The method of claim 3, wherein
   (b-1) the cavity is a human bladder;
   and further including:
   (a-2) concentrating, prior to step (b), a photoactivating drug in diseased cells in the bladder wall for treatment and destruction of the diseased cells;
   and wherein
   (e-2) substantially the entire inner bladder wall is irradiated in step (e).

6. The method of claim 5, further including:
   (a-3) providing the catheter, in step (a), with a flexible stem having an upper distal end to which the balloon is attached and through an inner lumen of which stem the light transmission fiber and diffuser tip of step (d) pass.

7. The method of claim 6, further including the steps of:

(g) providing at least one drainage port in fluid communication with the inner lumen of the stem; and
(h) draining urine from the bladder through the drainage port.

8. The method of claim 7 wherein
(e-3) the light is laser radiation and
(d-1) the fiber is quartz.

9. The method of claim 3, further including:
(a-2) providing, in step (a), at least one segment of the balloon which is opaque so that sections of the cavity underlying the at least one opaque segment will not be irradiated in step (e).

10. The method of claim 3, further including the steps of:
(a-2) concentrating, prior to step (b), a photoactivating drug in diseased cells in the cavity wall for treatment and destruction of the diseased cells; and
(g) measuring the concentration of photoactivating drug present in the cavity wall by measuring, with the at least one optical sensing fiber at the wall of the balloon, a fluorescent spectrum emitted by the drug during excitation by light.

11. A method for the uniform irradiation of the inner wall of a hollow cavity, including the steps of:
(a) providing a catheter having a deflated translucent balloon, the balloon having a wall:
(a-1) making the balloon, in step (a), of minimally distensible material;
(a-2) providing, in step (a), at least one optical sensing fiber at the wall of the balloon;
(b) inserting the catheter into the interior of the cavity;
(c) inflating the balloon until the balloon wall forms a generally spherical balloon configuration and distends at least one portion of an inner wall of the cavity to be irradiated into a contiguous and congruent generally spherical cavity configuration;
(c-1) the cavity being a human viscus, at least one portion of which cavity is formed in step (c) into a nearly perfectly spherical cavity configuration;
(d) inserting a light transmission fiber having a light diffuser tip into the catheter so that the tip is positioned at a center of the inflated balloon and, hence, automatically positioned at a uniform distance from the at least one portion of the cavity wall to be irradiated;
(e) transmitting light through the transmission fiber out the tip
(e-1) whereby light of uniform intensity irradiates the at least one portion of the cavity wall; and
(f) monitoring with the sensing fiber the cumulative light does to which the sensing fiber and, hence, the cavity wall are exposed.

12. A method for the uniform irradiation of the inner wall of a hollow cavity, including the steps of:
(a) providing a catheter having
(a-1) a deflated translucent balloon, the balloon having a wall, and
(a-2) at least one optical sensing fiber at the wall of the balloon;
(b) inserting the catheter into the interior of the cavity;
(c) inflating the balloon until the balloon wall forms a semi-rigid predetermined balloon configuration and distends at least one portion of an inner wall of the cavity to be irradiated into a contiguous and congruent cavity configuration;
(d) inserting a light transmission fiber having a light diffuser tip into the catheter so that the tip is positioned at a center of the inflated balloon and, hence, automatically positioned at a uniform distance from the at least one portion of the cavity wall to be irradiated;
(e) transmitting light through the transmission fiber out the tip
(e-1) whereby light of uniform intensity irradiates the at least one portion of the cavity wall; and
(f) monitoring with the sensing fiber on the wall of the cavity the light to which the sensing fiber and, hence, the cavity wall are exposed.

13. The method of claim 12 wherein
(a-3) the balloon is made, in step (a), of minimally distensible material and
(c-1) the cavity is a human viscus, at least one portion of which cavity is formed in step (c) into a cavity configuration which is at least a section of a nearly perfect sphere.

14. The method of claim 13, further including:
(a-4) providing, in step (a), a transparent minimally distensible center tube extending the length of the balloon through the center of the balloon for positioning the tip at the center of the balloon when the balloon is inflated in step (c).

15. The method of claim 12, further including the steps of:
(a-3) concentrating, prior to step (b), a photoactivating drug in diseased cells in the cavity wall for treatment and destruction of the diseased cells; and
(g) measuring the concentration of photoactivating drug present in the cavity wall by measuring, with the at least one optical sensing fiber at the wall of the balloon, a fluorescent spectrum emitted by the drug during excitation by light.

16. The method of claim 12, further including:
(a-3) providing, in step (a), at least one segment of the balloon which is opaque so that sections of the cavity underlying the at least one opaque segment will not be irradiated in step (e).

17. A method of treating and causing necrosis of diseased cells on the inner wall of a urinary bladder without over-treating healthy bladder cells, in which diseased cells a photoactivating drug has previously been concentrated, including the steps of:
(a) providing a catheter having
(a-1) a deflated translucent balloon of minimally distensible material,
(a-2) at least one optical sensing fiber in the material of the balloon,
(a-3) a clear minimally distensible center tube extending the length of the balloon through the balloon center, and
(a-4) a flexible stem having an upper distal end to which the balloon is attached, the stem having an inner lumen;
inserting the catheter into the interior of the bladder;
(c) inflating the balloon until it forms a semi-rigid balloon sphere and distends the inner wall of the bladder into a contiguous and congruent bladder sphere;
(d) inserting a laser light transmission fiber having an isotropic light diffuser tip into the inner lumen of the stem of the catheter so that the tip is positioned at the spherical center of the balloon and, hence, automatically positioned at the spherical center of the distended bladder;

(e) transmitting laser light radiation through the transmission fiber out the tip; and (f) monitoring with the sensing fiber the cumulative light dose to which the bladder wall is exposed (f-1) whereby laser light of uniform intensity irradiates the bladder, causing a photochemical reaction of the drug and destroying the diseased cells without over-irradiating healthy bladder cells.

18. The method of claim 17, further including the steps of:

(f-2) exciting, as part of step (f), the photoactivating drug by light; and (g) measuring the concentration of photoactivating drug present in diseased cells by measuring, with the at least one optical sensing fiber in the material of the balloon, a fluorescent spectrum emitted by the drug during the excitation by light.

19. A method for the uniform irradiation of the inner wall of a hollow cavity, including the steps of:

(a) providing a catheter having a deflated translucent balloon, the balloon having a wall;

(b) inserting the catheter into the interior of the cavity;

(c) inflating the balloon until the balloon wall forms a spherical balloon configuration and distends at least one portion of an inner wall of the cavity to be irradiated into a contiguous and congruent spherical cavity configuration;

(d) inserting a light transmission fiber having a light diffuser tip into the catheter so that the tip is positioned at a center of the inflated balloon and, hence, automatically positioned at a uniform distance from the at least one portion of the cavity wall to be irradiated; and (e) transmitting light through the transmission fiber out the tip (e-1) whereby light of uniform intensity irradiates the at least one portion of the cavity wall.

* * * * *